(12) United States Patent
Klemm

(10) Patent No.: US 10,657,403 B2
(45) Date of Patent: May 19, 2020

(54) MEDICAMENT DOSAGE DETERMINATION

(71) Applicant: SANOFI-AVENTIS DEUTSCHLAND GMBH, Frankfurt am Main (DE)

(72) Inventor: Thomas Klemm, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 18 days.

(21) Appl. No.: 15/542,508

(22) PCT Filed: Jan. 12, 2016

(86) PCT No.: PCT/EP2016/000036
§ 371 (c)(1),
(2) Date: Jul. 10, 2017

(87) PCT Pub. No.: WO2016/113127
PCT Pub. Date: Jul. 21, 2016

(65) Prior Publication Data
US 2018/0268236 A1    Sep. 20, 2018

(30) Foreign Application Priority Data

Jan. 12, 2015  (EP) .................................... 15150747

(51) Int. Cl.
*G06K 9/00*    (2006.01)
*A61M 5/315*   (2006.01)
(Continued)

(52) U.S. Cl.
CPC ........... *G06K 9/00993* (2013.01); *A61M 5/24* (2013.01); *A61M 5/3155* (2013.01);
(Continued)

(58) Field of Classification Search
CPC .. A61M 2005/3126; A61M 2205/3306; A61M 2205/3553; A61M 2205/3561;
(Continued)

(56) References Cited

U.S. PATENT DOCUMENTS

2013/0197445 A1\* 8/2013 Schabbach ......... A61B 5/14532
604/189
2014/0194826 A1\* 7/2014 Nielsen ................... A61M 5/24
604/189

FOREIGN PATENT DOCUMENTS

| WO | WO 2011/117212 | 9/2011 |
| WO | WO 2014/023763 | 2/2014 |
| WO | WO 2014/173768 | 10/2014 |

OTHER PUBLICATIONS

International Preliminary Report on Patentability in International Application No. PCT/EP2016/000036, dated Jul. 18, 2017, 7 pages.
(Continued)

*Primary Examiner* — Manuchehr Rahmjoo
(74) *Attorney, Agent, or Firm* — Fish & Richardson P.C.

(57) ABSTRACT

A data collection device includes a camera and a processing arrangement configured to capture at least two images of a medicament dose indicator of a medicament delivery device in each of the at least two images the processing arrangement identifies a displayed dosage using a first character identification technique, in each of the at least two images, determines whether the displayed dosages in the images are different and, if not, identifies at least one character in the images using a second character identification technique and determines the medicament dosage amount indicated by the medicament dose indicator based thereon. The first character recognition technique may be, for example, an optical pattern recognition or correlation, may be less computationally intensive than the second character recognition technique, for example, an optical character recognition (OCR).

(Continued)

In another embodiment, the first and second character recognition techniques are different OCR processes.

10 Claims, 10 Drawing Sheets

(51) Int. Cl.
*A61M 5/24* (2006.01)
*G06T 7/00* (2017.01)
*G06K 9/03* (2006.01)
*G06K 9/62* (2006.01)
*A61M 5/31* (2006.01)

(52) U.S. Cl.
CPC ........... *A61M 5/31525* (2013.01); *G06K 9/00* (2013.01); *G06K 9/03* (2013.01); *G06K 9/6201* (2013.01); *G06T 7/97* (2017.01); *A61M 2005/3126* (2013.01); *A61M 2205/3306* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/50* (2013.01); *A61M 2205/502* (2013.01); *A61M 2205/6072* (2013.01); *A61M 2205/6081* (2013.01); *G06K 2209/01* (2013.01); *G06K 2209/03* (2013.01)

(58) Field of Classification Search
CPC .. A61M 2205/3569; A61M 2205/3584; A61M 2205/3592; A61M 2205/50; A61M 2205/502; A61M 2205/6072; A61M 2205/6081; A61M 5/24; A61M 5/31525; A61M 5/3155; G06K 2209/01; G06K 2209/03; G06K 9/00; G06K 9/00993; G06K 9/03; G06K 9/6201; G06T 7/97
See application file for complete search history.

(56) References Cited

OTHER PUBLICATIONS

International Search Report and Written Opinion in International Application No. PCT/EP2016/000036, dated May 13, 2016, 9 pages.

\* cited by examiner

MEDICAMENT DOSAGE DETERMINATION

CROSS-REFERENCE TO RELATED APPLICATIONS

This application is a U.S. national stage application under 35 USC § 371 of International Application No. PCT/EP2016/000036, filed on Jan. 12, 2016, which claims priority to European Patent Application No. 15150747.2, filed on Jan. 12, 2015, the entire contents of which are incorporated herein by reference.

TECHNICAL FIELD

The present disclosure relates to data collection from a medicament delivery device. In particular, the present disclosure relates to a method and a device for determining a medicament dose.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dosage window or display of the insulin pen. The dose is then injected by inserting the needle into a suited skin portion and pressing an injection button of the insulin pen.

To be able to monitor insulin injection, for instance to prevent false handling of the insulin pen or to keep track of the doses already applied, it is desirable to measure information related to a condition and/or use of the injection device, for example, one or more of the injected insulin type, dose and timing of the injection, in a manner that is reliable and accurate.

Data collection techniques may also be used for purposes other than monitoring insulin injections. For example, data may be collected in order to monitor injections of other medicaments, other medical activities, such as the taking of tablet medication by a patient or infusions, or for non-medical purposes, such as the monitoring of equipment and/or its operation in a home or industrial environment for safety reasons.

SUMMARY

According to one aspect, there is provided a method of recording a medicament dose by a data collection device, the method including capturing, by a camera of the data collection device, at least two images of a medicament dose indicator of a medicament delivery device, determining a current medicament dosage amount displayed by the medicament dose indicator in each of the at least two images using a first character identification technique, determining whether the determined current medicament dosage amounts are different and, in response to a determination that the displayed dosage amounts are not different in the at least two images, identifying at least one character in one of the at least two images using a second character identification technique and determining the medicament dosage amount indicated by the medicament dose indicator based on a result of said second character identification technique.

In such a method, the first character identification technique may be less computationally intensive than said second character identification technique. For example, the first character identification technique may determine a correlation between the images and stored reference images, while the second character identification technique may analyse and identify individual characters and, where necessary, combine the identified characters to provide a result.

The use of first and second character recognition techniques, where the first technique is less computationally intensive than the second technique, allows processing resources within the data collection device to be used more efficiently, by reducing the processing used to identify characters while a dose is being programmed into the medicament delivery device. This may, in turn, reduce energy requirements. Where the data collection device is powered by a battery, such reduced energy requirements may result in a longer battery life.

The method may include displaying a current dosage amount based on a result of said first character identification technique. In embodiments where the data collection device includes a display arranged to show a current dose programmed into the medicament delivery device in real time, the use of a first character identification technique with reduced processing requirements may allow the current dose to be displayed quickly.

The second character identification technique may include optical character recognition (OCR).

The first character identification technique may include an optical pattern recognition, or optical pattern correlation, technique in which a correlation between the at least one character and one or more templates stored in the data collection device is determined.

The first character identification technique may include OCR. For example, the first character identification technique may be a first OCR process, while the second character identification is a second OCR process that is different from the first OCR process. In such an example, processing requirements may be reduced since the second OCR process, used to determine a finalized medicament dosage, may be more detailed and, therefore, more computationally intensive, than the first OCR process carried out during programming of the medicament dosage. For example, the first OCR process may analyze the image at a lower resolution than the second OCR process. Alternatively, or additionally, the second OCR process may perform a number of iterations exceeding a number of iterations performed in the first OCR process and/or The medicament delivery device may be an injector pen comprising a movable component for selecting said amount of medicament to be dispensed.

The above aspect also provides a computer program comprising computer-readable instructions which, when executed by a processor of a data collection device, causes said data collection device to perform a method according to any of the preceding claims.

The above aspect further provides a data collection device including a camera and a processing arrangement configured to capture at least two images of a medicament dose indicator of a medicament delivery device using said camera, in each of the at least two images, determine a current medicament dosage amount displayed by the medicament dose indicator using a first character identification technique, determine whether the current medicament dosage amounts shown in the at least two images are different, and in response to a determination that the displayed dosage amounts are not different, identify at least one character in the images using a second character identification technique and determining the medicament dosage amount indicated by the medicament dose indicator based on a result of said second character identification technique.

The first character identification technique may be less computationally intensive than said second character identification technique.

The data collection device may include a display and be configured to display a current dosage amount based on a result of said first character identification technique The second character identification technique may include optical character recognition.

The first character identification technique may include determining a correlation between the at least one character and one or more reference images stored in the data collection device, in an optical pattern recognition or optical pattern correlation process. Such pattern recognition/correlation techniques can provide a robust character identification method, based on selecting a reference image with a minimum deviation from the obtained image of the at least one character. Alternatively, the first character identification technique may include optical character recognition.

The data collection device may include a mating arrangement to allow it to be releasably, or permanently, attached to the medicament delivery device. Alternatively, the data collection device may be a handheld or wearable electronic device. In such a device, the processing arrangement may be configured to adjust scale of the at least two images before identifying the at least one character using the first character identification technique.

The processing arrangement may be configured to combine multiple images captured by said camera, said multiple images having different exposure levels, to provide said image with a high dynamic range. The obtaining of such a high dynamic range image may provide a higher quality image and/or improved contrast, facilitating optical character recognition of the at least one character.

The processing arrangement may be configured to identify a color of at least one component of the medicament dispensing device and to determine a type of said medicament based on said color. The identification of the color may, optionally, include determining a color balance measurement based on reference color information provided on the medicament delivery device. This may allow information regarding medicament type to be obtained automatically, without specific input from the user, potentially improving reliability of the information obtained.

The medicament delivery device may be an injector pen that includes a movable component for selecting said amount of medicament to be dispensed.

BRIEF DESCRIPTION OF THE FIGURES

Example embodiments of the disclosure will now be described with reference to the accompanying figures, of which:

FIG. 1b shows a perspective view of some detail of the drug delivery device of FIG. 1a;

FIG. 8 shows an example of a binarized digits corresponding to digits displayed in the dosage window;

FIGS. 9 and 10 show diagrammatically further examples of digits that may be displayed in the dosage window;

DETAILED DESCRIPTION

In the following, embodiments of the present disclosure will be described with reference to an insulin injection device. The present disclosure is however not limited to such application and, as noted herein above, may equally well be deployed with injection devices that eject other medicaments, or with other types of medicament delivery devices.

Figure 1A:
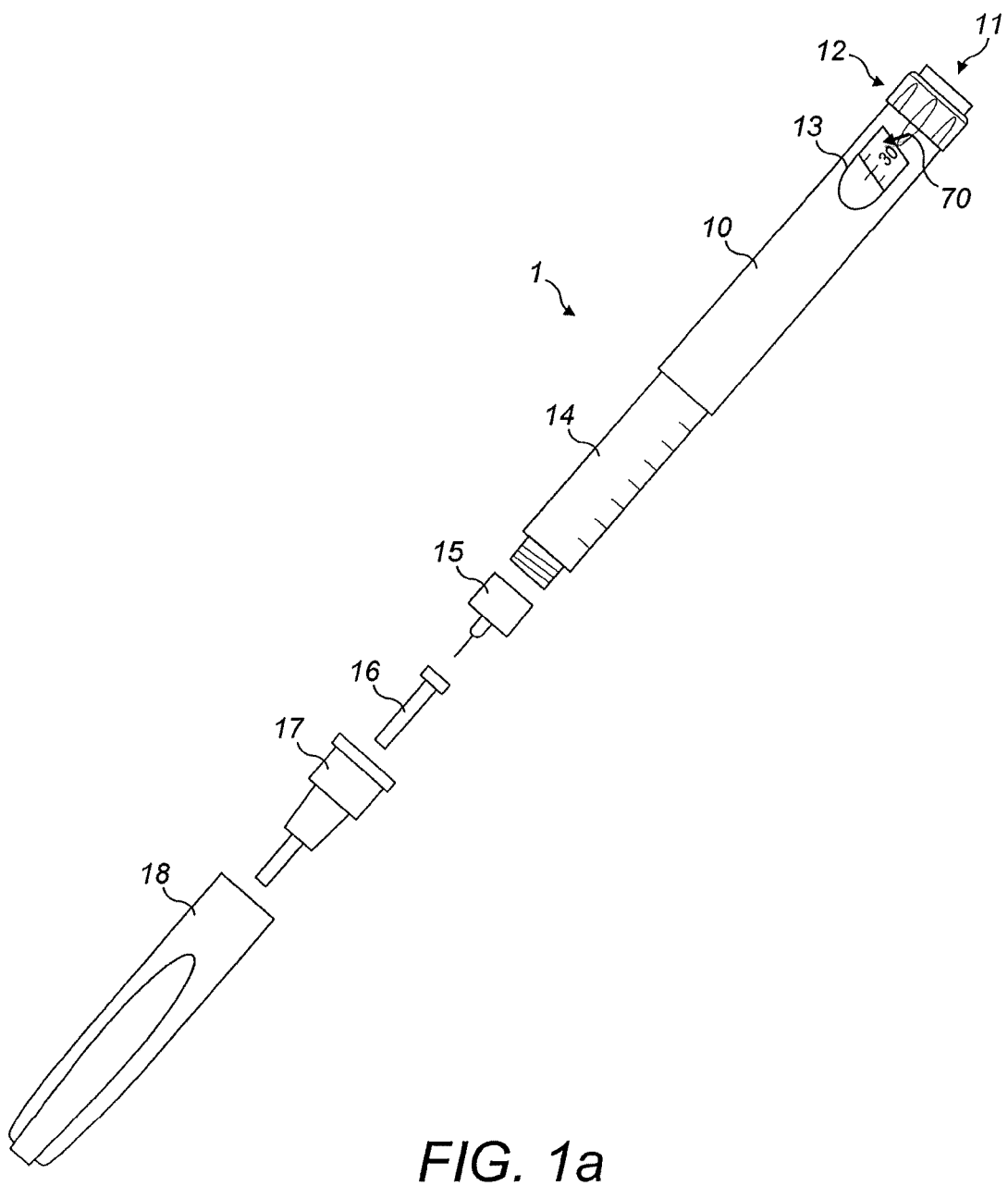
FIG. 1a shows an exploded view of a drug delivery device.

FIG. 1a is an exploded view of a medicament delivery device. In this example, the medicament delivery device is an injection device 1, such as Sanofi's SoloSTAR® insulin injection pen.

The injection device 1 of FIG. 1a is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1a. It should be noted that the selected dose may equally well be displayed differently.

The dosage window 13 may be in the form of an aperture in the housing 10, which permits a user to view a limited portion of a number sleeve 70 that is configured to move when the dosage knob 12 is turned. In order to facilitate taking images of the numbers displayed in the dosage window 13, the number sleeve 70 may have a matte surface.

In this particular embodiment, the injection device 1 includes a component that provides information identifying a type of medicament loaded in the injection device 1. In this particular example, the number sleeve 70 may have a background color that corresponds to the medicament type. In other embodiments, one or more parts of the injection device, such as an injection button 11 or the dosage knob 12, may be formed of a material having a color that corresponds to the medicament. Optionally, a part of an insulin container (not shown) within the injection device 1 may include a colour-coded portion that indicates a medicament type and may be viewable through the dosage window 13. The information identifying the medicament may additionally, or alternatively, be encoded into a barcode, QR code or the like. The information identifying the medicament may also be in the form of a black and white pattern, a color pattern or shading. In other embodiments, the information may alternatively, or additionally, be included in a label provided on the housing 10, using text or color. For example, such a label may have a background, or include a shaded element such as a border having a color that corresponds to a particular type of medicament that is provided in the injection device. Alternatively, or additionally, the label may include a RFID tag or similar device that stores such information about the medicament.

Turning the dosage knob 12 causes a mechanical click sound to provide acoustic feedback to a user. The numbered sleeve 70 mechanically interacts with a piston in insulin container 14. When needle 15 is stuck into a skin portion of a patient, and then injection button 11 is pushed, the insulin dose displayed in the dosage window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 1B:
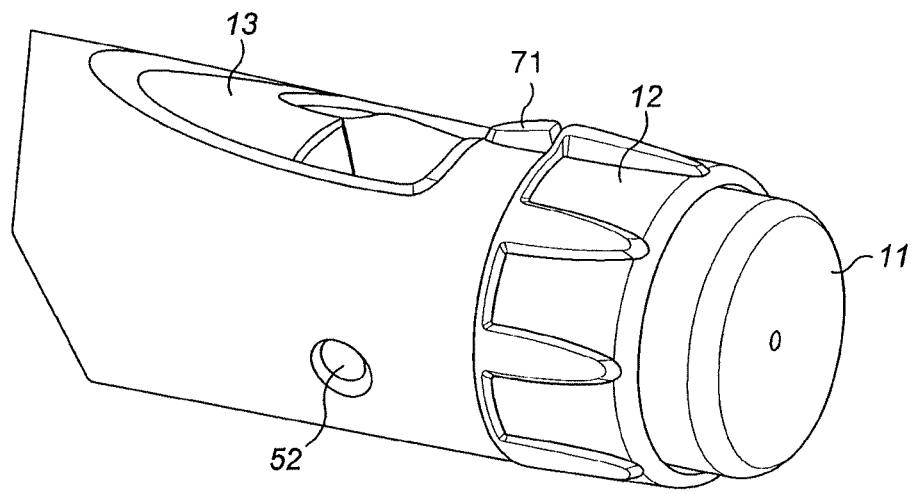

FIG. 1b is a close-up of the end of the injection device 1, showing a locating rib 71 that is located between the viewing window 13 and the dosage knob 12.

Figure 2A:
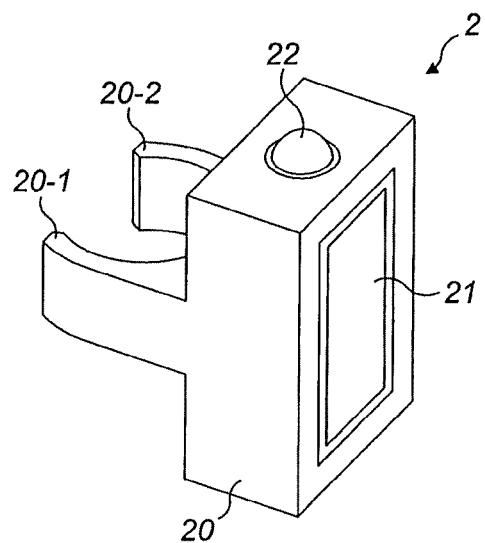
FIG. 2a depicts an example data collection device configured to be releasably attached to the drug delivery device of FIGS. 1a and 1b.

FIG. 2a is a schematic illustration of an embodiment of a supplementary device 2 to be releasably attached to injection device 1 of FIG. 1. Supplementary device 2 comprises a housing 20 with a mating unit configured and embrace the housing 10 of injection device 1 of FIG. 1, so that supplementary device 2 sits tightly on housing 10 of injection device 1, but is nevertheless removable from injection device 1, for instance when injection device 1 is empty and has to be replaced. FIG. 2a is highly schematic, and details of the physical arrangement are described below with reference to FIG. 2b.

Supplementary device 2 contains optical and acoustical sensors for gathering information from injection device 1. At least a part of this information, for instance a selected dose (and optionally a unit of this dose), is displayed via display unit 21 of supplementary device 2. The dosage window 13 of injection device 1 is obstructed by supplementary device 2 when attached to injection device 1.

Supplementary device 2 further comprises at least one user input transducer, illustrated schematically as a button 22. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

Figure 2B:
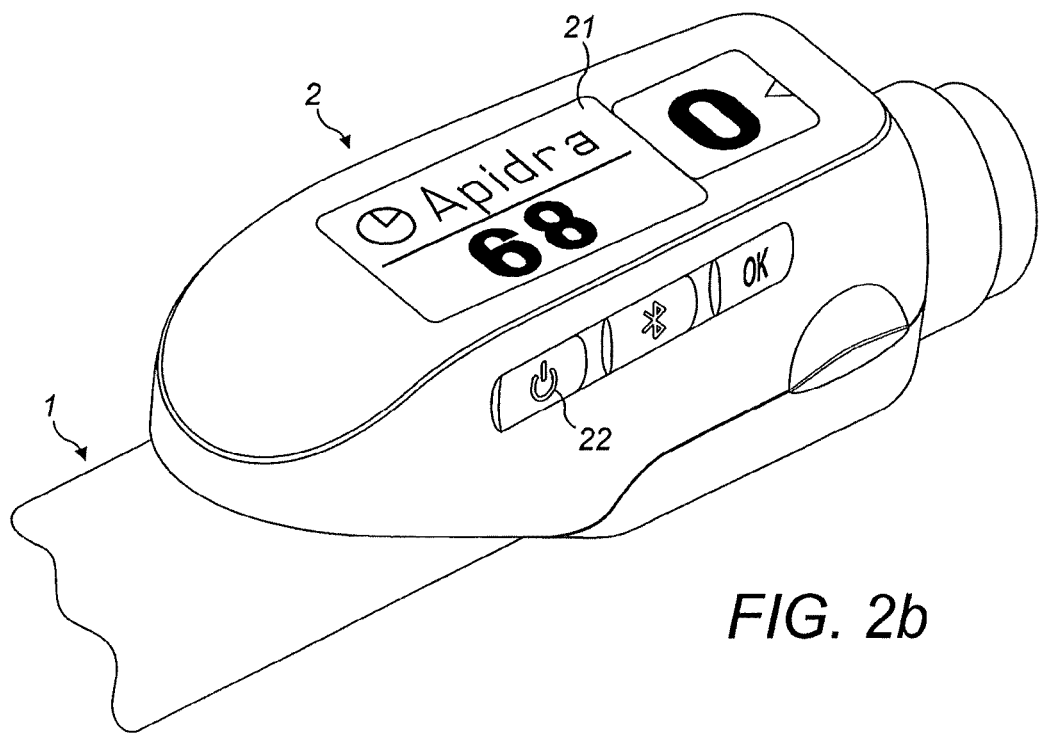
FIG. 2b depicts an example data collection device configured to be releasably attached to the drug delivery device of FIGS. 1a and 1b.

FIG. 2b is a schematic illustration of a second embodiment of a supplementary device 2 to be releasably attached to injection device 1 of FIG. 1. Supplementary device 2 comprises a housing 20 with a mating unit configured and embrace the housing 10 of injection device 1 of FIG. 1, so that supplementary device 2 sits tightly on housing 10 of injection device 1, but is nevertheless removable from injection device 1.

Information is displayed via display unit 21 of supplementary device 2. The dosage window 13 of injection device 1 is obstructed by supplementary device 2 when attached to injection device 1.

Supplementary device 2 further comprises three user input buttons or switches. A first button 22 is a power on/off button, via which the supplementary device 2 may for instance be turned on and off. A second button 33 is a communications button. A third button 34 is a confirm or OK button. The buttons 22, 33, 34 may be any suitable form of mechanical switch. These input buttons 22, 33, 34 allow a user to turn on/off supplementary device 2, to trigger actions (for instance to cause establishment of a connection to or a pairing with another device, and/or to trigger transmission of information from supplementary device 2 to another device), or to confirm something.

Figure 2C:
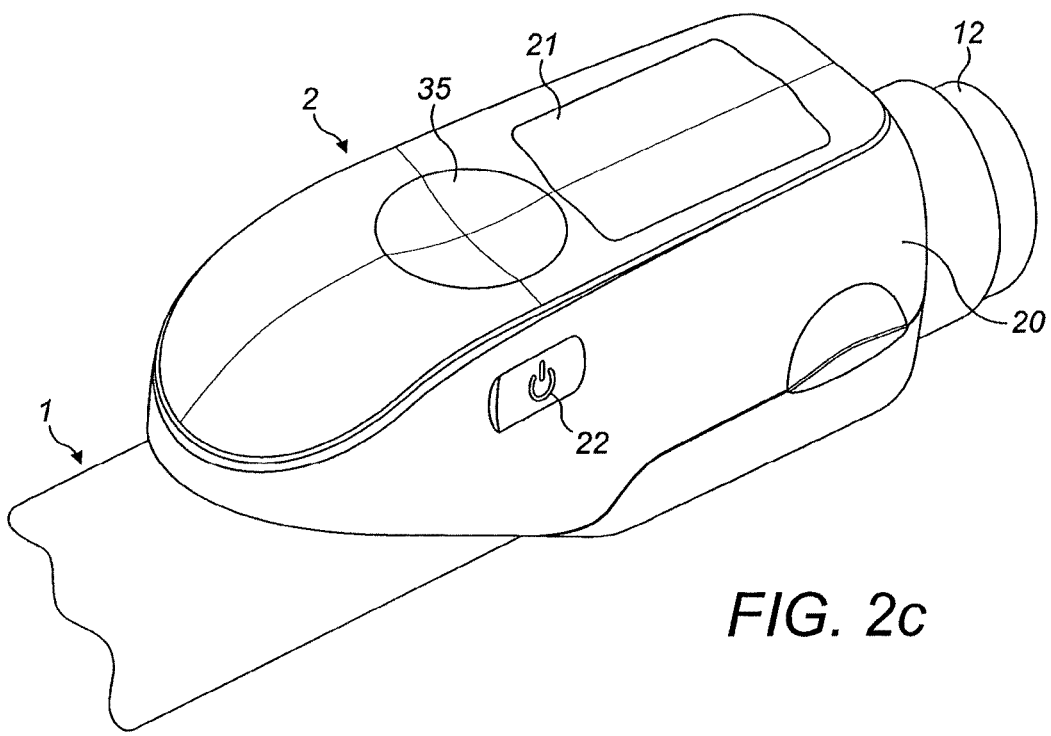
FIG. 2c depicts an example data collection device configured to be releasably attached to the drug delivery device of FIGS. 1a and 1b.

FIG. 2c is a schematic illustration of a third embodiment of a supplementary device 2 to be releasably attached to injection device 1 of FIG. 1. Supplementary device 2 comprises a housing 20 with a mating unit configured to embrace the housing 10 of injection device 1 of FIG. 1, so that supplementary device 2 sits tightly on housing 10 of injection device 1, but is nevertheless removable from injection device 1.

Information is displayed via display unit 21 of the supplementary device 2. The dosage window 13 of injection device 1 is obstructed by supplementary device 2 when attached to injection device 1.

Supplementary device 2 further comprises a touch-sensitive input transducer 35. It also comprises a single user input button or switch 22. The button 22 is a power on/off button, via which the supplementary device 2 may for instance be turned on and off. The touch sensitive input transducer 35 can be used to trigger actions (for instance to cause establishment of a connection to or a pairing with another device, and/or to trigger transmission of information from supplementary device 2 to another device), or to confirm something.

Figure 3:
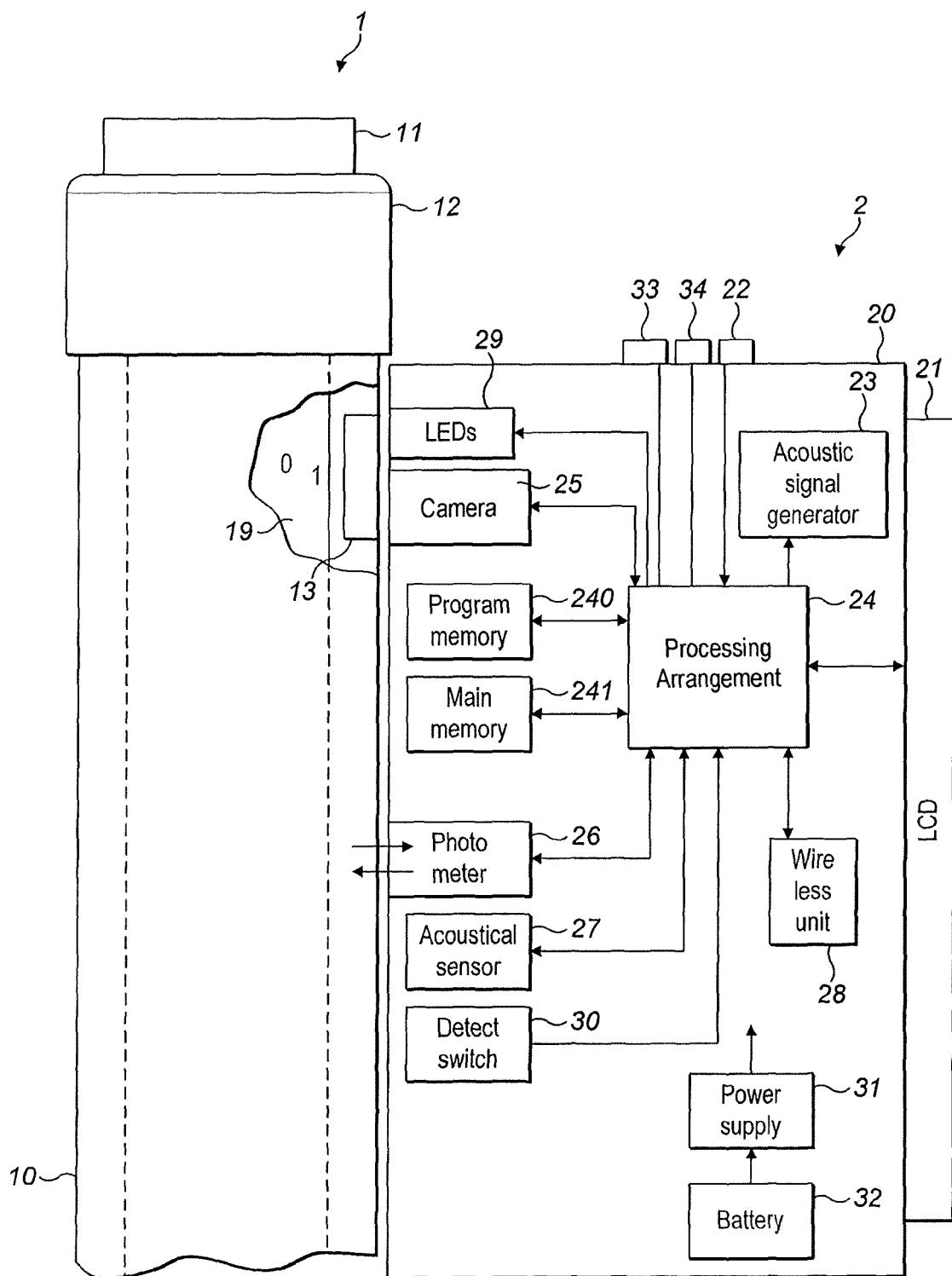
FIG. 3 is a block diagram of the data collection of FIG. 2a when attached to the injection device of FIG. 1.
Figure 3:
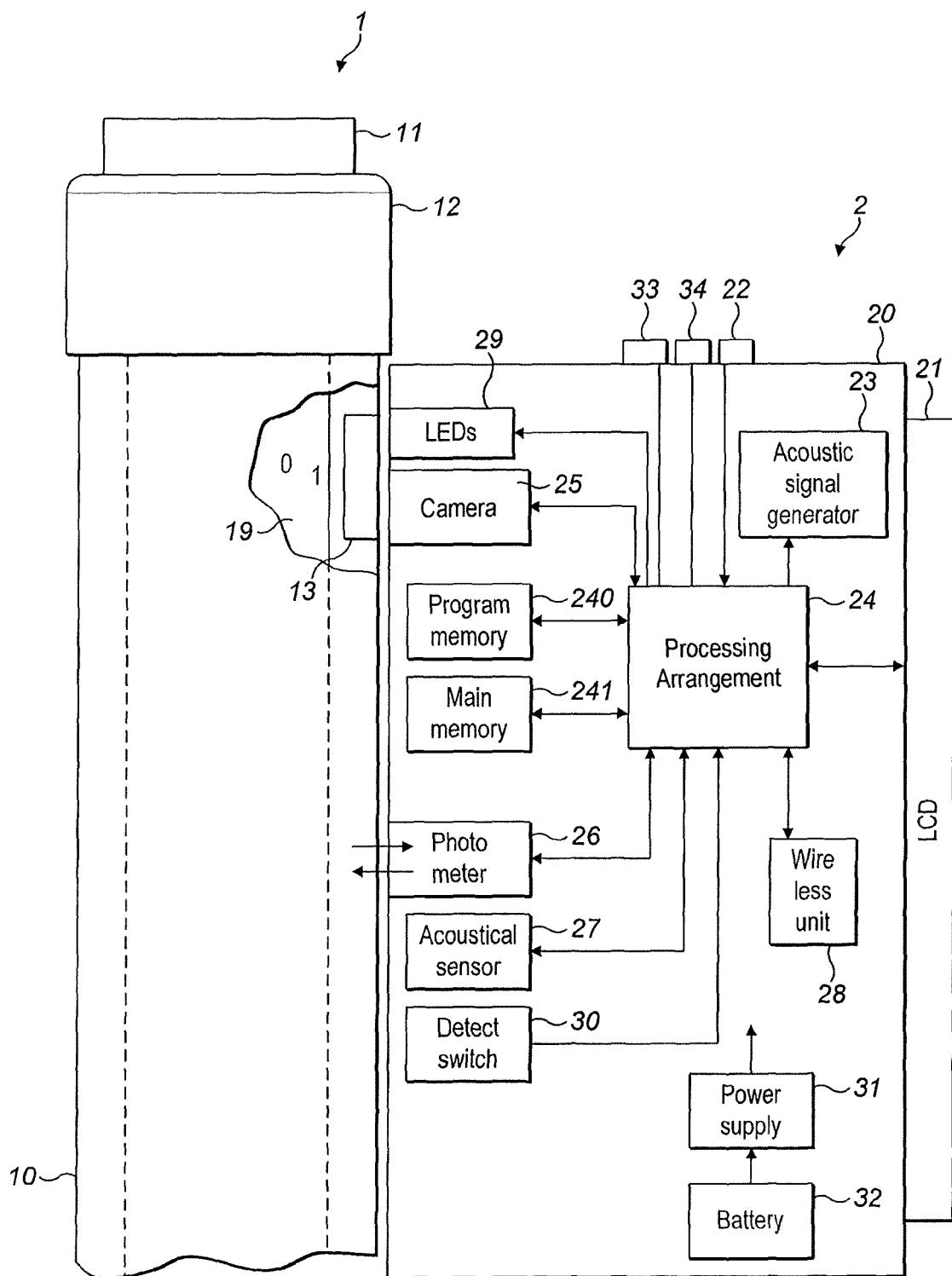

FIG. 3 shows a schematic view of the supplementary device 2 of FIG. 2a in a state where it is attached to injection device 1 of FIG. 1.

With the housing 20 of supplementary device 2, a plurality of components are contained. These are controlled by a processing arrangement 24, which comprise one or more processors, such as a microprocessor, a Digital Signal Processor (DSP), Application Specific Integrated Circuit (ASIC), Field Programmable Gate Array (FPGA) or the like. Processing arrangement 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

In embodiments such as those shown in FIG. 2b, processing arrangement 24 interacts with a first button 22, via which supplementary device 2 may for instance be turned on and off. A second button 33 is a communications button. The second button may be used to trigger establishment of a connection to another device, or to trigger a transmission of information to another device. A third button 34 is a "confirm or OK" button. The third button 34 can be used to acknowledge information presented to a user of supplementary device 2. In embodiments such as those shown in FIG. 2c, two of the buttons 33, 34 may be omitted. Instead, one or more capacitive sensors or other touch sensors are provided.

Processing 24 controls a display unit 21, which is, in this example, is a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processing arrangement 24 also controls an optical sensor 25, embodied as an Optical Character Recognition (OCR) reader, that is capable of capturing images of the dosage window 13, in which a currently selected dose is displayed (by way of numbers, characters, symbols or glyphs present on the sleeve 19 contained in injection device 1, which numbers are visible through the dosage window 13). OCR reader 25 is further capable of recognizing characters (e.g. numbers) from the captured image and to provide this information to processor 24. Alternatively, unit 25 in supplementary device 2 may only be an optical sensor, e.g. a camera, for capturing images and providing information on the captured images to processing arrangement 24. Then processing arrangement 24 is responsible for performing OCR on the captured images.

Processing arrangement 24 also controls light-sources such as light emitting diodes (LEDs) 29 to illuminate the dosage window 13, in which a currently selected dose is displayed. A diffuser may be used in front of the light-sources, for instance a diffuser made from a piece of acrylic glass. Furthermore, the optical sensor may comprise a lens system, for instance including two aspheric lenses. The magnification ratio (image size to object size ratio) may be smaller than 1. The magnification ratio may be in the range of 0.05 to 0.5. In one embodiment the magnification ratio is 0.15.

Processing arrangement 24 further controls a photometer 26, that is configured to determine an optical property of the housing 10 of injection device 1, for example a color or a shading. The optical property may only be present in a specific portion of housing 10, for example a color or color coding of sleeve 19 or of an insulin container comprised within injection device 1, which color or color coding may for instance be visible through a further window in housing 10 (and/or in sleeve 19). Information on this color is then provided to processing arrangement 24, which may then determine the type of injection device 1 or the type of insulin contained in injection device 1 (e.g. SoloStar Lantus with purple color and SoloStar Apidra with blue color). Alternatively, a camera unit may be used instead of photometer 26, and an image of the housing, sleeve or insulin container may then be provided to processing arrangement 24 to determine the color of the housing, sleeve or insulin container by way of image processing. Further, one or more light sources may be provided to improve reading of photometer 26. The light source may provide light of a certain wavelength or spectrum to improve color detection by photometer 26. The light source may be arranged in such a way that unwanted reflections, for example by dosage window 13, are avoided or reduced. In an example embodiment, instead of or in addition to photometer 26, a camera unit may be deployed to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may, for instance, indicate a type of the injection device and/or the medicament, and/or further properties (for instance, a expiration date).

Figure 4:
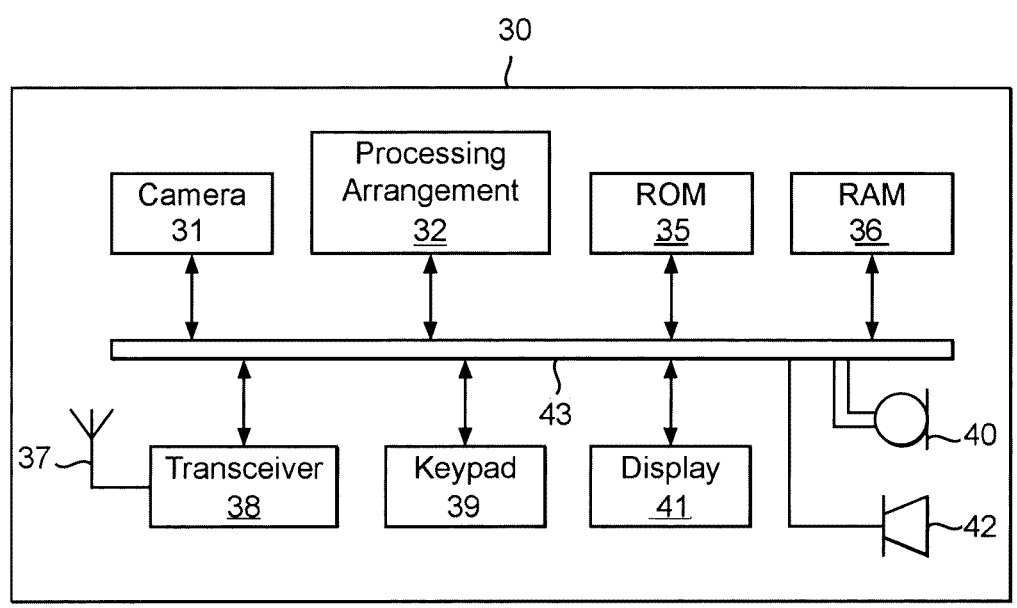
FIG. 4 is a block diagram of a data collection.

FIG. 4 is a block diagram of a supplementary device 30, according to another embodiment of the disclosure, that may be used to collect data, such as insulin type, dosage and timing of injection, from the injection device 1 of FIG. 1. In the particular example shown in FIG. 2a, the supplementary device 30 is a cellphone, or "smartphone", although other types of device, such as a wearable computing device or a tablet computer, may be used. The supplementary device 30 is equipped with a built-in camera 31, and a processing arrangement 32 including one or more processors, such as a microprocessor, a Digital Signal Processor (DSP), Application Specific Integrated Circuit (ASIC), Field Programmable Gate Array (FPGA) or the like. The cellphone 30 also includes memory units 35, 36, including a main memory 35 and a program memory 36, which can store software for execution by the processing arrangement 32. The supplementary device 30 also includes communications equipment 37, 38, such as an antenna 37 and a transceiver 38, to permit bi-directional communication with one or more of a cellphone network, a personal area network, a local wireless network and the Internet. The supplementary device 30 further includes an input arrangement 39, 40, such as a keypad 39 and microphone 40, and an output arrangement 41, 42, such as a speaker 41 and display 42. In some embodiments, the input arrangement 39, 40 may include provide a keypad 39 in a touch-screen that utilizes some or all of the display 42. The supplementary device 30 also includes a communications bus 43 allowing for communication between the camera 31, processing arrangement 32, memory units 33, 34, communications equipment 37, 38, input arrangement 39, 40 and output arrangement 41, 42.

In the example shown in FIG. 4, the software stored in the memory units 35, 36 of the supplementary device 30 includes software application or "app" that, when executed by the processing arrangement 32, causes the supplementary device 30 to take an image of the injection device 1 and to process the image to obtain data regarding the type of medicament in the injection device 1 and/or the selected dose.

An example method according to an embodiment of the disclosure, using the supplementary device 2, will now be described with reference to FIGS. 5 to 11.

Starting at step s5.0, an image of at least the dosage window 13 of the injection device 1 is obtained (step s5.1), by controlling the camera 25 of the supplementary device 2 to capture an image. In other embodiments, where the supplementary device 30 is hand-held or wearable, the distance between the injection device 1 and the camera 31 and the orientation of the dosage window 13 are not fixed. In view of this, the processing arrangement 22 adjusts the scale of the image so that the size of the characters displayed within the dosage window 13 are within a predetermined range.

Next, information regarding the type of medicament is obtained (step s5.2) by identifying a color of a part of the injection device 1 that indicates the medicament type from the image. In this particular embodiment, the background of the number sleeve 70 of the injection device 1 is configured to provide reference color information to allow one or more color in the image to be identified correctly. For example, the background of the printed numbers may be used to provide a white balance level for calibrating the color of the components of the injection device 1 as shown in the image. In another embodiment, the color background of the number sleeve 70 may be used to indicate the type of medicament loaded into the injection device 1 and, optionally, reference color information may be provided elsewhere on the injection device 1. Alternatively, the information regarding the type of medicament may be obtained by identifying a character from a part of the image including the label (not shown) or extracting and interpreting a barcode (not shown) from a part of the image, for example, using optical character recognition.

A second image of the dosage window 13 is obtained using the camera 25 (step s5.3).

The processing unit 24 then determines a medicament dosage that is displayed in the dosage window 13 shown in the second image. In this example, the characters of the number sleeve 70 shown in the dosage window 13 in the second image are identified using an optical pattern recognition, or optical pattern correlation, algorithm performed by the processing arrangement 24 (step s5.4), by scanning over stored reference images of numerical characters corresponding to those on the number sleeve 70 and comparing them to the second image. The reference images may be stored in a look up table in the program memory 240. By determining which of the reference images exhibits the highest overlap with the dosage window 13 shown in second image, the at least one character and its location within the dosage window 13 may be identified.

In this manner, the optical pattern recognition performed in step s5.4 may determine the current dosage amount without having to identify individual characters displayed in the dosage window 13. For example, where a currently programmed dosage amount is "10", the dosage may be determined based on a correlation between the image and a reference image of the number "10", without recognizing the individual digits "1" and "0".

Optionally, further checks on the result of the pattern recognition process can be made, based on redundancy and checking the exposure of the image, to monitor and improve performance.

The currently dosage is then determined, based on the result of the optical pattern recognition process and the processing arrangement 24 determines whether the dosage amount shown in the dosage window 13 is changing (step s5.5) by comparing the result with a result of optical pattern recognition performed on a previous image, where available. A difference in the images corresponding to movement of the number sleeve 70 would indicate a change in the currently programmed dosage. Such a difference may be demonstrated by a change in identity of the at least one character between two images, or from changes in the location of the at least one character in the dosage window 13 between the two images.

If it is determined that the dosage is changing (step s5.5), then the current dosage is displayed by the display 21 (step s5.6) and steps s5.3 to s5.5 are repeated to capture a new image (step s5.3), determine a currently displayed dosage amount shown in the new image (step s5.4) and determine whether the dosage is changing (step s5.5).

If a determination cannot be made, for example, if the result of the optical pattern recognition process (step s5.4) is unclear, or if there are no previous images to compare to the image captured in step s5.3, then steps s5.3 to s5.5 are repeated to capture a new image (step s5.3), determine a currently displayed dosage amount shown in the new image (step s5.4) and determine whether a change in dosage has occurred (step s5.5).

If it is determined that the dosage is not changing (step s5.5), then one or more characters in the newest image are identified using OCR (step s5.7).

Alternatively, a further image may be obtained and then used in the analysis performed in step s5.7. The further image may be obtained by taking multiple images of the dosage window 13 at various exposure levels and combining them, to provide a high dynamic range (HDR) image, in order to provide an improved quality image for analysis.

In this embodiment, the optical character recognition (step s5.7) includes pre-processing by the processing arrangement 24 to assess and, if required, improve image data quality by executing the following steps:

Defective and bad pixel correction
Light correction
Distortion
Jitter

It is noted that the pre-processing is an optional feature. The app may be designed to perform to the required standard without pre-processing of the image.

The pre-processing performed by the processing arrangement 24 may also adjust the image by correcting skew of the characters displayed in the dosage window 13 based on the orientation of the injection device 1 relative to the camera and/or any slanting of the characters displayed in the dosage window 13. For instance, the numbers in the dosage window 13 might be slanted for ease of recognition and positioning by a user, but may be easier to decode by the supplementary device 2 if the slant is removed.

Such adjustments may be based on an analysis of features of the injection device 1 of predetermined shape and/or size. For example, the processing arrangement 24 may identify the dosage window 13, a logo (not shown) on the injection device 1 and/or other features of the injection device 1 in the image and, based on information regarding the expected shape and/or size of those features, correct for skew of text and numbers included in the image.

Figure 5:
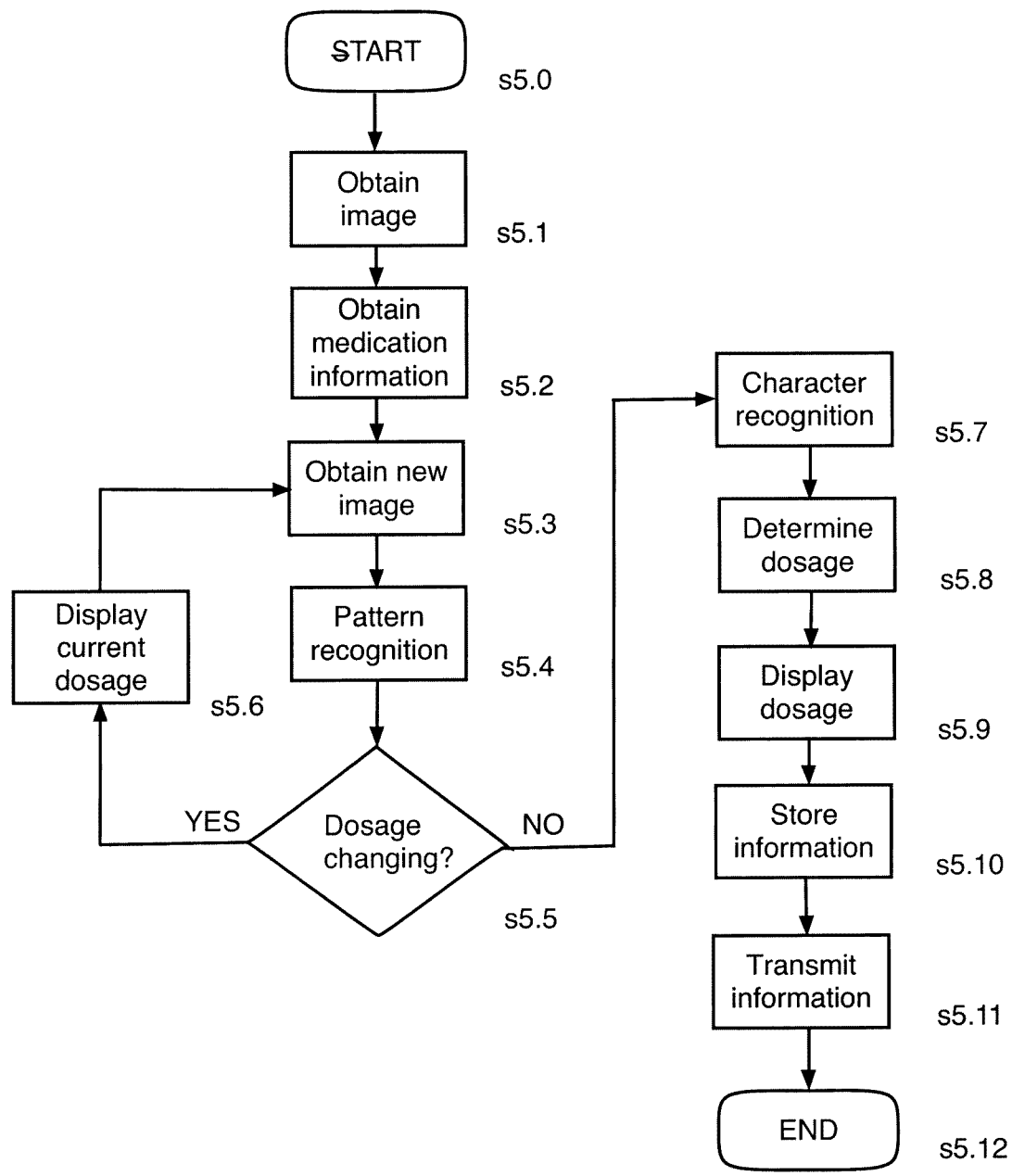
FIG. 5 is a flowchart of a medicament dosage determination method.
Figure 6:
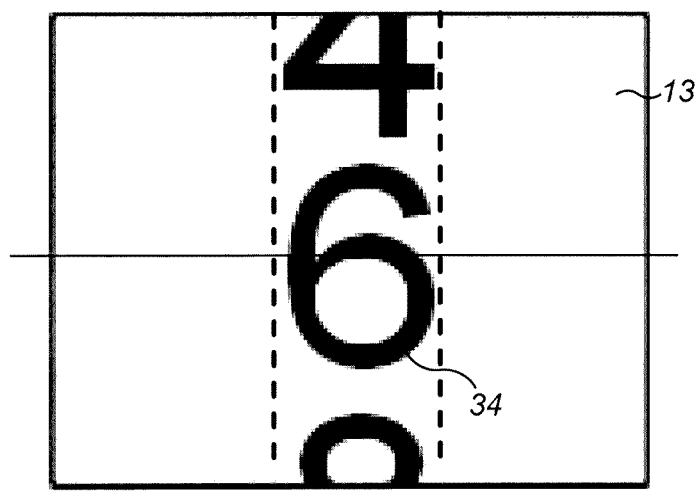
FIGS. 6 and 7 each show a portion of a dosage window of the drug delivery device of FIG. 1a, with examples of digits that may be displayed.
Figure 7:
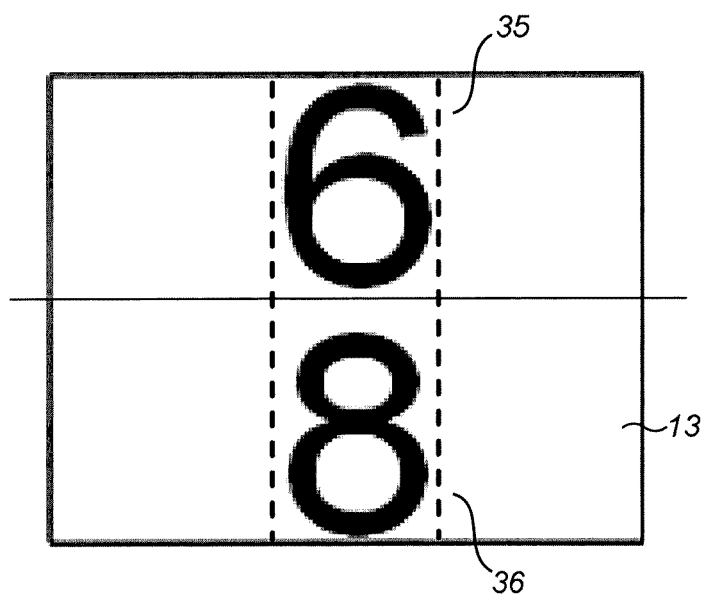
Figure 10:
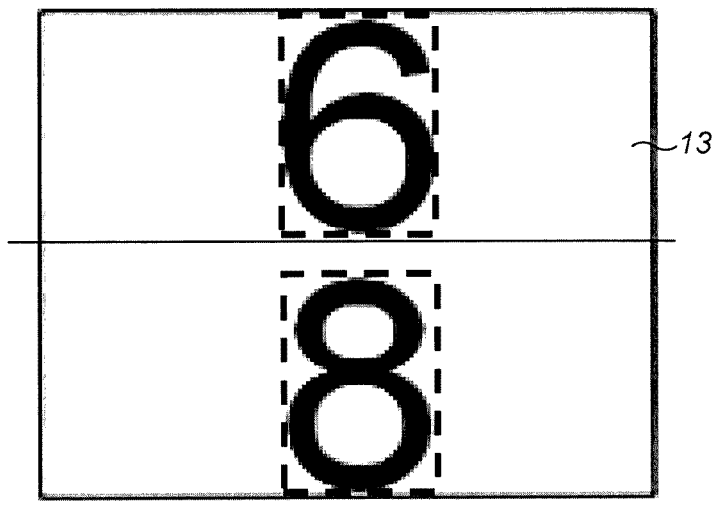

FIGS. 6 and 7 depict a portion of the dosage window 13, showing examples of digits that may be shown. In FIG. 6, a dosage has been dialed into the injection device 1 such that the a digit 34, in this case the number 6 indicating 6 IU, is displayed centrally in the dose window 13. In FIG. 5, a dosage of 7 IU has been dialed into the injection device 1 such that digits 35, 36, representing the numbers 6 and 8 respectively, are both displayed in the dose window 13 and the space between these numbers occupies the central region of the dose window 13. In this particular embodiment, the processing arrangement 24 is configured to execute an algorithm allowing both of the situations depicted in FIGS. 6 and 7 to be decoded accurately.

The OCR process comprises the steps of:
Binarization
Segmentation
Pattern matching
Position calculation There may, in some embodiments, be two OCR algorithms that are operated in parallel to provide increased reliability of the OCR process. In such embodiments, the two OCR algorithms have the same input image and are intended to provide the same output. They both perform similar steps however the individual methods used in each step may vary. These two OCR algorithms may differ in one of the binarization, segmentation, pattern matching and position calculation steps or in more than one of these steps. Having two OCR-parts which use different methods to provide the same result increases the reliability of the entire algorithm as the data has been processed in two independent ways.

In the OCR process, the color or greyscale image obtained from the camera 25 and adjusted as described above is converted into a purely black and white image 37, such as that depicted in FIG. 8, through a binarization process. In an example where dark numbers are presented on a bright background in the dosage window, the black and white image would indicate the presence of digits 38, 39 with black pixels and the absence of digits with white pixels, as shown in the example of FIG. 8. In some embodiments a fixed threshold is used to separate between black and white pixels. Pixels that have a value at or above the threshold become white, pixels below the threshold become black in the binarized picture. A high threshold will lead to artefacts (black parts in white areas), whereas a low threshold has the risk that in some cases parts of digits are missing. In some embodiments, the threshold is chosen so that in no case are parts of digits are missing because the algorithm is in general robust against artefacts (i.e. an accurate OCR process can be performed in the presence of some artefacts). In tests where an image was analyzed using 256 grey values, a threshold value of 127 showed good results.

The use of a fixed threshold is possible where light correction has been performed, for example, in the pre-processing. The combination of the light correction and the fixed threshold is similar to a windowed mean binarization. A windowed mean binarization compares the pixel-value with the mean value of the pixels of the area where it is located. Performing the light correction step before the distortion and slant correction steps means that more information is available to be used for the OCR process, which has been shown to yield better results on the edges and corners of the picture.

Alternatively, the Otsu threshold method may be applied to the captured greyscale image to produce a binary image similar to the binarized image 37 shown in FIG. 8. In some alternative embodiments, the binarization may be omitted and the OCR part of the algorithm may be performed on the captured color or greyscale image.

Segmentation is then performed. The goal of this part of the algorithm is to determine the exact location of each visible or partly visible number in the image. To achieve this, the algorithm defines the boundaries of the visible digits by finding the edges of the digits. This is generally accomplished in two steps, which may be performed in any order. Referring again to FIGS. 6 and 7, the processing arrangement 24 may perform a "vertical projection" in which the pixel columns making up the binarized image 37 are analyzed. Each pixel column is analyzed individually and the sum of the number of black pixels in each column is computed. In some embodiments, only a pixel column having zero black pixels defines the edge of a number. Alternatively, a low threshold for the number of black pixels may be set to account for dirt, scratches and other disturbances. Difference values for adjacent columns are calculated and the boundary having the greatest difference represents the edge of the number. Additionally, the pixel content of overlapping groups of columns (e.g. three adjacent columns) may be calculated to aid in determining the horizontal edges of the numbers.

The processing arrangement 24 then performs a "horizontal projection" in which the pixel rows making up the binarized image 37 are analyzed. This proceeds in a similar manner to that as described above with regard to the vertical projection.

The expected result of the horizontal projection is added to that of the vertical projection such that the edges of the visible numbers are identified. The processing arrangement 22 may be pre-programmed with the expected height (in pixel rows) of a full number, and so is able to recognize the presence of partially visible numbers.

In another embodiment, the "horizontal projection" and the "vertical projection" may be based on an analysis where the sum of white pixels is computed, provided that the expected number of white pixels in each row and column is known.

Knowing the exact location allows for using only the part of the image which represents the visible number or numbers for the next steps in the OCR process. By this any impact of other objects besides the number, e.g. dirt, scratches and other disturbances, can be reduced. Further, the total number of pixels to be processed in subsequent steps, e.g. in the pattern matching step, is also reduced. This helps reducing resource requirements. This also helps increasing performance. In addition, knowing the exact location also supports determining the vertical position relative to the center of the image.

The next step in the OCR process is to select one of the visible numbers to be decoded and identified. This is done by designating one of the numbers as the "primary digit row". The primary digit row is selected based on which visible number has the greatest height. This is because all of the numbers printed on the sleeve 70 have approximately the same height and it can be assumed that the number having the greatest height will be fully visible and therefore easy to decode with a high degree of certainty. In the example shown in FIG. 9, the number "6" has a greater height than the partially visible numbers above and below and so is selected as the primary digit row. In the example shown in FIG. 10, both the numbers "6" and "8" are fully visible and have the same height. In this case, the uppermost number is selected as the primary digit row. The primary digit row is the number which is subsequently used to determine the dose dialed into the injection device 1.

A standard injection device 1 for self administration of insulin can inject any number of units of medicament from 1 to 80 IU. Therefore, in order to properly decode the number identified as the primary digit row, it must be determined whether the number consists of one or two digits. The processing arrangement 24 therefore performs a series of steps in order to determine whether each number consists of one or two digits, and in the latter case, to separate the digits from each other. The processing arrangement 24 may use the column pixel information previously calculated for this purpose. In the example shown in FIG. 11, a dosage of 9 IU of medicament has been dialed into the injection device 1. The expected results of the horizontal and vertical projections are shown. The number "10" is of greater height than the number "8" and is therefore selected as the primary digit row.

After this the processing arrangement 24 determines whether the selected primary digit row is wider than a pre-defined "maximum digit width" value. The processing arrangement 24 may be pre-programmed with information relating to the expected size of the numbers in the captured images, so that a maximum expected width for a single digit can be defined. In order to increase reliability, the maximum width may be set as a small number of pixel columns more than the widest number. If the width of the primary digit row is the maximum digit width or less, it is assumed that the row contains a single digit. If the primary digit row is too wide to be a single digit, then a second vertical projection is then performed on the primary digit row (rather than on the whole image). In addition, the expected width of each individual digit may be used to predict the point at which the separation should occur.

Figure 11:
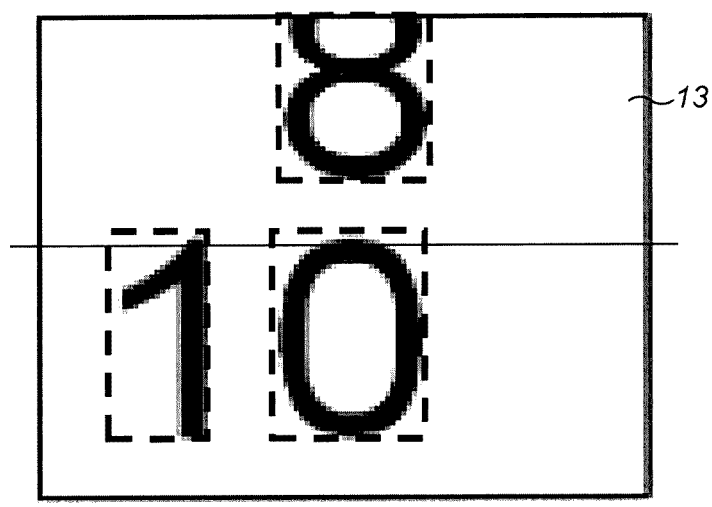
FIG. 11 shows a further example of digits that may be displayed in the dosage window where a primary digit row contains two digits.

The exemplary field of view shown in FIG. 11 is a diagrammatic representation in which the numbers are well spaced. In other arrangements, the numbers may be displayed quite close together in the dosage window, owing to limited available space and the need for the numbers to be readable to a user. Thus, after binarization, the two digits making up the number may not be cleanly separated, i.e. there may not be a column having no black pixels between the two digits. This is the case in the exemplary binarized image shown in FIG. 8, in which the "7" and "4" of the upper digits 37 do not have a pixel column between them containing no black pixels. In this case, the expected width of each individual digit is again used to predict the point at which the separation should occur. If the predicted column contains black pixels, then the deviations of this column from adjacent columns are calculated to determine the best separation point. In this situation, as it is not clear whether the black pixels in the chosen separating column belong to the left or right digit, they are ignored. This has been shown to have a minimal effect on the reliability of the OCR process to correctly identify the digits.

A pattern matching process is then performed to identify the digits in the primary digit row by comparing the digits to the reference images stored in program memory 240. In a straightforward approach the pattern matching could be performed on a pixel-by-pixel basis. However, this may require high computing power and may be prone to position variation between the image and the reference image. Where reference images are used, the processing arrangement 24 may be configured to perform other types of manipulation on the images numbers, for example by changing the size of one or more digits, cropping the numbers to a defined pixel area and shearing numbers printed in a italic font into an upright position. These manipulations may be performed before a pattern matching comparison with the reference images. Alternatively, as discussed above, these manipulations may be performed in preprocessing before the binarization process. Additional shading, distortion and exposure correction may also be performed.

In some other embodiments, a feature recognition process is performed. Features may be horizontal, vertical or diagonal lines, curves, circles or closed loops etc. Such features may be recognized in the image of the selected number and compared with templates.

In yet further embodiments, the pattern matching algorithm may be based on a vector comparison process. For example, the templates may be in the form of vectors describing the position and length of each line (continuous run) of black pixels. In one example, the position and length relate to the absolute position in the respective line. In another example, the position and length relate to a vertical line extending through the center of the template. The captured binary image of each digit may similarly be converted into vectors and compared with each stored template in turn to find the best match. When comparing the vectors of the captured image with a particular digit template, any deviations result in a penalty being applied for the likelihood of a match between the image and that template. The magnitude of the penalty may depend on the number of missing or extra black pixels in the image compared to the template. After the digit image has been compared with each template and all of the penalties have been applied a decision is made as to which digit is present. In good optical conditions, the correct template will have a very low penalty, while all other templates will have a high penalty. If the primary digit row consists of two digits, this process is performed on both digits and the processing arrangement 24 can then combine the outcomes to produce a final result for the number.

Special measures may exist for certain digits. For example, "1" deviates substantially in width from all other digits resulting in common misdetections. To counter this, if a binary image of a digit is wider than the expected width of "1", then it receives an additional detection penalty when being compared with the stored vector template of "1".

In some exceptional cases, if the confidence level in the result of the pattern matching of the primary digit row is below a certain threshold (e.g. 99%), then the processing arrangement 24 may perform a second pattern matching process on one or more of the other visible or partially visible numbers. Since the order of the numbers is known, this second pattern matching can act as a check that the first pattern matching returned the correct result.

If the confidence level in the result is still not high enough, then another image may be obtained using the camera 25 and step s5.7 repeated.

Once the digit or digits of the primary digit row have been successfully identified, a weighting function is applied in order to determine a dose dialled into the injection device 1 (step s5.8). To formulate the weighting function, the vertical position of the primary digit row relative to the center of the dosage window 13 may be determined. This may be done by calculating the offset of the middle pixel row comprising the primary digit row relative to a pixel row representing a center line of the dosage window 13 in the image.

For example, in some embodiments the optical sensor comprises a rectangular 64×48 array of photosensitive elements. The resulting binary image is a pixel array having these same dimensions. The 24th and/or 25th pixel row may be designated as the central row of the image. The position of the middle pixel row comprising the primary digit row is determined. The offset, in pixel rows, between the middle pixel row comprising the primary digit row and the central row or rows of the image is then calculated. This offset may be positive or negative depending on the direction of the offset. The offset is converted into a fraction by dividing it by the distance (in pixel rows) between successive numbers before being applied to the determined numbers accordingly. The offset therefore allows for determining the rotational position of the number relative to the sensor. If the central pixel row of the primary digit row is the same as the central pixel row of the image, then the offset is zero and the position is equal to the primary digit row number. However, there is likely to be some offset in most circumstances.

The distance between successive numbers printed on the numbered sleeve 70 is constant, since the numbers represent a dose which is related to a discrete mechanical movement of the injection device mechanism. Therefore, the distance (in pixel rows) between successive numbers in the captured image should also be constant. The expected height of the numbers and spaces between the numbers may be pre-programmed into the app. As an example, the expected height of each numbers may be 22 pixels and the expected height of the spaces between the numbers may be 6 pixels. Therefore, the distance between the central pixel rows of successive numbers would be 28 pixels.

Continuing this example, if the pixel rows are numbered sequentially from the top to the bottom of the image, the application of the weighting function may be defined mathematically as:

$$\text{Position} = \text{primary digit row number} + [2 \times \text{offset}/(\text{expected height of number} + \text{expected height of space})]$$

Where offset=image row number corresponding to the centre of the dosage window−primary digit row central row number Thus, if the primary digit row is in the upper half of the image, then the offset is positive and if the primary digit row is in the lower half of the image, then the offset is negative. For example, if the number shown in the primary digit row is "6" and the offset is zero, then the calculated position would be:

$$\text{Position} = 6 + [2 \times 0/(28)] = 6$$

Thus a result of "6" would be returned as expected.

In another example, where 75 IU are dialled into the injection device 1, if the top number, "74", is selected as the primary digit row and there is a positive offset of 11 pixel rows according to the equation above, and again assuming a combined number/space height of 28 pixels, the calculated position would be:

$$\text{Position} = 74 + [2 \times 11/(28)] = 74.79$$

This result is then rounded up to the nearest whole number, to give a position determination of "75" as expected.

The skilled person will appreciate that the above described weighting function and position determination represents only one example and that numerous other calculation methods may be used to arrive at the same result. The skilled person would also appreciate that the above described mathematical calculation may be modified and improved to reduce the computation time. Thus the exact form of the weighting function is not essential to a definition of the present disclosure.

In some injection devices, due to space restrictions and the need for the numbers to be of a certain size, only even numbers are presented in the dosage window 13. In some other injection devices, only odd numbers may be displayed. However, any number of units of medicament can be dialled into the injection device 1. In other injection devices, both even and odd numbers may be presented and it may be possible to dial half-unit doses into the injection device. The injection device may be limited to a maximum dialled dose of 80 IU. Alternatively, only every 3rd, 4th or 5th number may be displayed and doses between the numbers may be indicated by tick marks. In view of this, the app may include instructions for controlling the processing arrangement 24 to identify the numbering sequence used in the injection device 1. For example, the user may be prompted to enter information regarding the injection device 1 via button 34 or a keypad 39, where provided, or information obtained from the image, for example from the text or a barcode on the label (not shown) may be used. The app may include a look-up table or other information indicating the numbering sequences used for various injection devices 1. The processing arrangement 24 may then determine the selected dose based on both OCR data and the appropriate numbering sequence for the injection device 1. Alternatively, or additionally, a modified form of the weighting function may be used, as the height of the numbers and size of the space between the numbers may also be modified.

The method may optionally include post-processing, such as performing sanity checks and hysteresis calculations. Alternatively, the result of the OCR process may be finalized without post-processing.

The determined medicament dosage is then displayed on the display 21 (step s5.9).

The information obtained from the image may then be stored in the program memory 240 of the supplementary device 2 (step s5.10) and/or transmitted to another device via a network, such as a cellphone network, personal area network or the Internet, using the communications equipment 25, 26 (step s5.11), completing the process (step s5.12). Optionally, information regarding a timestamp of the image may also be stored and/or transmitted. In this manner, the administration of medicament to a patient may be recorded and monitored.

Figure 12:
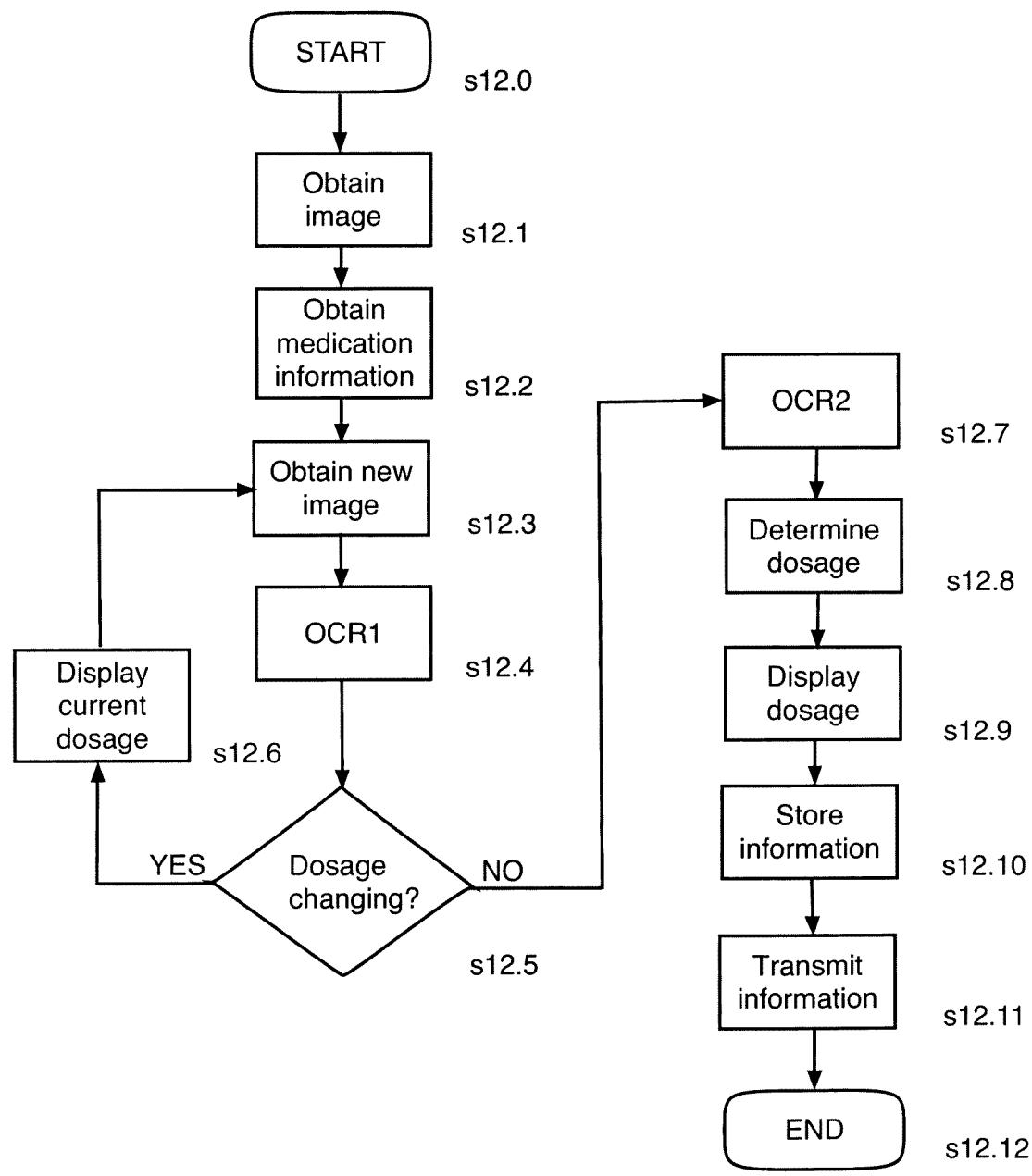
FIG. 12 is a flowchart of a medicament dosage determination method.

FIG. 12 depicts a method for determining a medicament dosage, according to another embodiment of the disclosure, also using the supplementary device 2.

Starting at step s12.0, an image of at least the dosage window 13 is obtained using the camera 25 (step s12.1) and medication information is determined based on the image (step s12.2), as described above in relation to FIG. 5, steps s5.1 and s5.2.

A second image is then obtained using the camera 25 (step s12.3) and then a currently displayed medicament dosage is determined using a first optical character recognition technique (OCR1) (step s12.4). In this particular example, OCR1 is based on Hidden Markov Models (HMM).

The currently dosage is then determined, based on the result of OCR1, and the processing arrangement 24 determines whether the dosage amount shown in the dosage window 13 is changing (step s12.5) by comparing the result with a result of optical pattern recognition performed on a previous image, where available. A difference in the images corresponding to movement of the number sleeve 70 would indicate a change in the currently programmed dosage. Such a difference may be demonstrated by a change in identity of the at least one character between two images, or from changes in the location of the at least one character in the dosage window 13 between the two images.

If it is determined that the dosage is changing (step s12.5), then the current dosage is displayed by the display 21 (step s12.6) and steps s12.3 to s12.5 are repeated to capture a new image (step s12.3), determine the currently displayed dosage amount shown in the new image (step s12.4) and determine whether a change in dosage has occurred between the new image and the previous image (step s12.5).

If a determination cannot be made, for example, if the result of the optical pattern recognition process (step s12.4) is unclear, or if there are no previous images to compare to the image captured in step s12.3, then steps s12.3 to s12.5 are repeated to capture and process a new image and determine whether the dosage is changing.

If it is determined that the dosage is not changing (step s12.5), then one or more characters in the newest image are identified using a second optical character recognition process OCR2 (step s12.7).

Alternatively, a further image may be obtained and then used in the analysis performed in step s12.7. For example, the further image may be obtained by taking multiple images of the dosage window 13 at various exposure levels and combining them, to provide a high dynamic range (HDR) image, in order to provide an improved quality image for analysis.

OCR2 may be carried out in the manner described above in relation to FIG. 5, step s5.7. Alternatively, OCR2 may be another optical character recognition process that differs from OCR1, such as a technique based on discrete cosine transforms (DCTs).

Once the one or more characters have been identified (step s12.7), the displayed dosage amount is determined (step s12.8), for example, by applying a weighting function as described above in relation to FIG. 5, step s5.8.

The method may optionally include post-processing, such as performing sanity checks and hysteresis calculations. Alternatively, the result of the OCR process may be finalized without post-processing.

The determined medicament dosage is then displayed on the display 21 (step s12.9) and, optionally, stored (step s12.10) and/or transmitted to another device (step s12.11), completing the process (step s12.12).

In the example method of FIG. 12, the first and second OCR processes OCR1, OCR2 are based on different algorithms. However, in other embodiments, the first and second OCR processes OCR1, OCR2 may differ in other manners, in addition to, or instead of, the type of algorithms used. For example, OCR1 and OCR2 may differ in terms of the resolution with which the images are analyzed, with OCR2 utilizing a higher resolution than OCR1. Alternatively, or additionally, OCR2 may include an iterative process, while OCR1 does not, or where OCR1 and OCR2 both include iterative processes, a greater number of iterations may be performed in OCR2 when compared with OCR1.

In the embodiments described above, different techniques are used to determine dosages during programming of the injection device 1, for example in step s5.4 of FIG. 5 and step 12.4 of FIG. 12, and to determine a finalized dosage, for example in step s5.7 of FIG. 5 and step 12.7 of FIG. 12. By using a less computationally intensive technique to determine dosages during programming of the injection device 1 (steps s5.4, s12.4), when compared with the technique used to determine a finalized dosage (steps s5.7, s12.7), fewer processing resources may be used during programming of the injection device 1 without compromising the accuracy and reliability of the finalized dosage determined at steps s5.9 and s12.9, allowing the processing resources and energy use of the supplementary device 2 to be used efficiently.

Alternatively, or additionally, the determination of the current dosage at steps s5.4 and s12.4 may be performed more quickly than the determination of the finalized dosage at steps s5.7 and s12.7, allowing the dosage shown on the display 21 to be updated quickly.

In one test example, a time interval between capturing an image and updating a dosage amount displayed by display 21 based on analysis of the captured image using an optical pattern recognition technique as in step s5.4 was between 200 and 250 ms. By way of contrast, the time interval between image capture and updating the display, when using an OCR technique based on HMM and DCT was 550 to 1000 ms, and more battery power was required.

While the embodiments above have been described in relation to collecting data from an insulin injector pen, it is noted that embodiments of the disclosure may be used for other purposes, such as monitoring of injections of other medicaments or other medical processes.

The invention claimed is:

1. A method of recording a medicament dose using a data collection device, the method comprising:
    capturing, by a camera of the data collection device, at least two images of a medicament dose indicator of a medicament delivery device;
    determining a current medicament dosage amount displayed by the medicament dose indicator in the at least two images using a first character identification technique, the first character identification technique comprising a first algorithm;
    displaying a current dosage amount based on a result of said first character identification technique;
    determining whether the current medicament dosage amounts in the at least two images are different; and
    in response to a determination that the current displayed dosage amounts are not different, identifying at least one character in one of the at least two images using a second character identification technique, the second character identification technique comprising a second algorithm that is different than the first algorithm, and determining the medicament dosage amount indicated by the medicament dose indicator based on a result of the second character identification technique, wherein the first character identification technique is less computationally intensive than the second character identification technique.

2. The method according to claim 1, wherein the second character identification technique comprises optical character recognition.

3. The method according to claim 1, wherein the first character identification technique comprises determining a correlation between the at least one character and a plurality of templates stored in the data collection device.

4. The method according to claim 1, wherein the medicament delivery device comprises an injector pen comprising a movable component for selecting the amount of medicament to be dispensed.

5. A non-transitory digital storage medium comprising computer-readable instructions which, when executed by a processor of a data collection device, causes the data collection device to:
    capture, by a camera of the data collection device, at least two images of a medicament dose indicator of a medicament delivery device;
    determine a current medicament dosage amount displayed by the medicament dose indicator in the at least two images using a first character identification technique;
    display a current dosage amount based on a result of said first character identification technique;
    determine whether the current medicament dosage amounts in the at least two images are different; and
    in response to a determination that the current displayed dosage amounts are not different, identifying at least one character in one of the at least two images using a second character identification technique, the second character identification technique comprising a second algorithm that is different than the first algorithm, and determining the medicament dosage amount indicated by the medicament dose indicator based on a result of the second character identification technique, wherein the first character identification technique is less computationally intensive than the second character identification technique.

6. A data collection device comprising:
a camera; and
a processing arrangement configured to:
capture at least two images of a medicament dose indicator of a medicament delivery device using the camera;
in each of the at least two images, determine a current medicament dosage amount displayed by the medicament dose indicator using a first character identification technique;
cause a current dosage amount based on a result of said first character identification technique to be displayed;
determine whether the current medicament dosage amounts are different in the at least two images; and
in response to a determination that the current displayed dosage amounts are not different, identifying at least one character in one of the at least two images using a second character identification technique, the second character identification technique comprising a second algorithm that is different than the first algorithm, and determining the medicament dosage amount indicated by the medicament dose indicator based on a result of the second character identification technique, wherein the first character identification technique is less computationally intensive than the second character identification technique.

7. The data collection device according to claim 6, comprising a display configured to display a medicament dosage amount based on a result of the first character identification technique.

8. The data collection device according to claim 6, wherein the second character identification technique comprises optical character recognition.

9. The data collection device according to claim 6, wherein the first character identification technique comprises determining a correlation between the at least one character and one or more templates stored in the data collection device.

10. The data collection device according to claim 6, wherein the processing arrangement is configured to identify a color of at least one component of the medicament dispensing device and to determine a type of the medicament based on the color.

* * * * *